United States Patent [19]

Millick, III

[11] 3,956,362

[45] May 11, 1976

[54] COOXIDATION PROCESS FOR THE PRODUCTION OF DIMETHYL TEREPHTHALATE

[75] Inventor: William H. Millick, III, Hockessin, Del.

[73] Assignee: Hercules Incorporated, Wilmington, Del.

[22] Filed: Oct. 4, 1973

[21] Appl. No.: 403,582

[52] U.S. Cl. .......................... 260/475 R; 260/524 R
[51] Int. Cl.$^2$.......................................... C07C 69/82
[58] Field of Search ................................ 260/475 R

[56] References Cited
UNITED STATES PATENTS 2,894,978   7/1959   Katzschmann .................. 260/475 R

*Primary Examiner*—Lorraine A. Weinberger
*Assistant Examiner*—Jane S. Myers
*Attorney, Agent, or Firm*—George H. Hopkins

[57] ABSTRACT

Disclosed is an improvement in the cooxidation process for making dimethyl terphthalate (DMT). In the cooxidation process an oxidate comprising monomethyl terephthalate and p-toluic acid is esterified with methanol to form a reaction mixture comprising DMT and methyl p-toluate, methyl p-toluate is separated from the reaction mixture, and p-xylene and said methyl p-toluate are cooxidized in the liquid phase with molecular oxygen to form more oxidate, which is esterified, etc. The improvement comprises separating p-toluic acid from part of the oxidate prior to esterifying the oxidate, and cooxidizing separated p-toluic acid with said p-xylene and said methyl p-toluate. This improvement results in a lesser quantity of oxidate subjected to esterification, and a reduction in the quantity of methyl p-toluate cooxidized with p-xylene.

7 Claims, 1 Drawing Figure

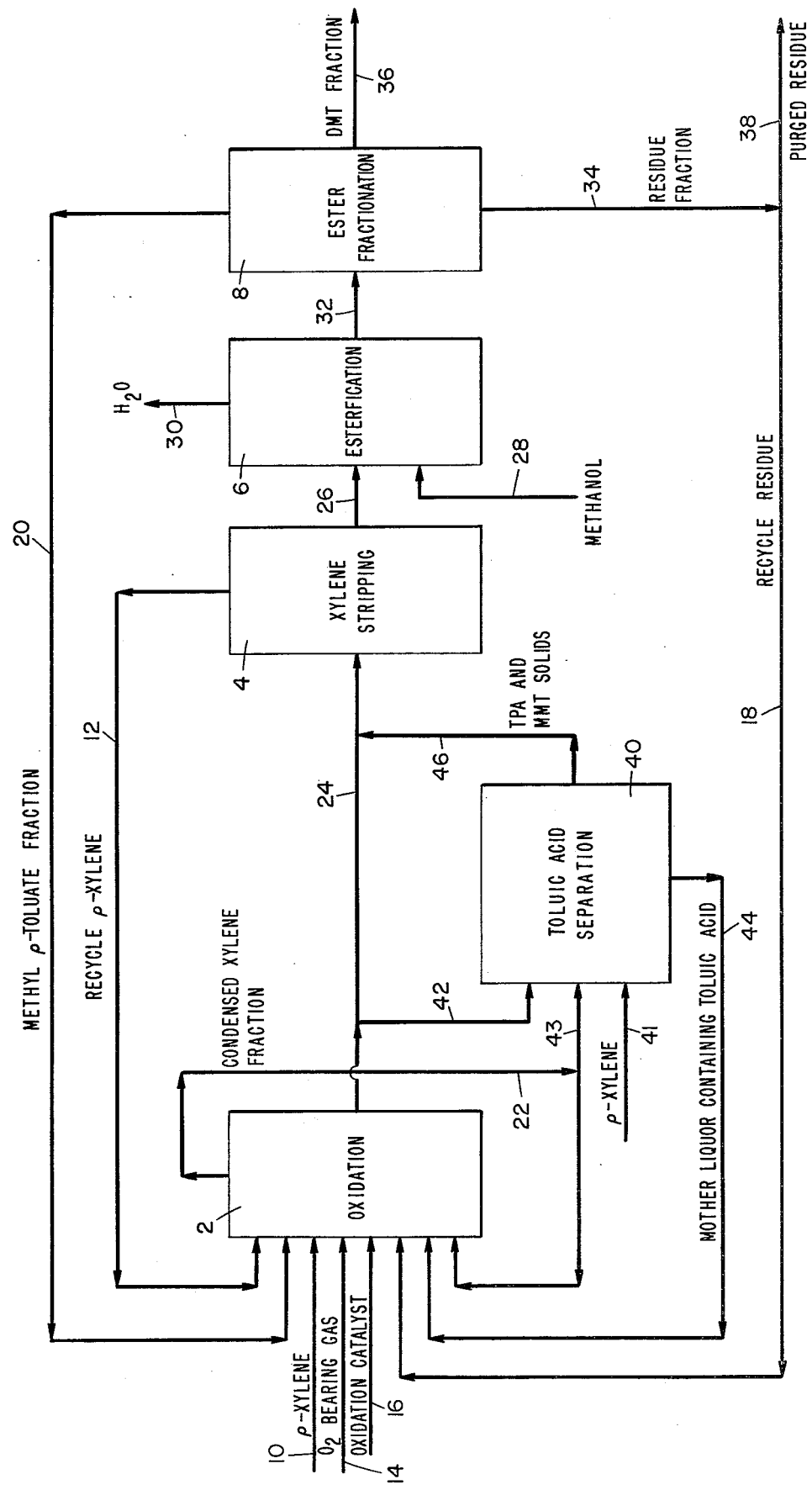

COOXIDATION PROCESS FOR THE PRODUCTION OF DIMETHYL TEREPHTHALATE

This invention is in the chemical arts. It relates to that branch of organic chemistry having to do with aromatic polycarboxylic acid esters and processes for making them.

Dimethyl terephthalate (herein DMT) is a well-known chemical of commercial importance. It is used in enormous quantities in the production of polyester polymers from which fibers and the like are made.

A classic process for making DMT comprises the steps of oxidizing p-xylene in the liquid phase with molecular oxygen to form p-toluic acid, esterifying the acid with methanol to form methyl p-toluate, oxidizing methyl p-toluate with molecular oxygen to form monomethyl terephthalate, and esterifying the monomethyl terephthalate with methanol to form DMT. This process can be carried out on a batch basis or continuously. Also, oxidation of p-xylene and methyl p-toluate with molecular oxygen is generally effected with an oxidation catalyst which in preferred embodiments also catalyzes the esterification reactions. Examples of oxidation catalyst disclosed in the art include cobalt or a salt thereof, manganese or a salt thereof, and both cobalt or a salt thereof and manganese or a salt thereof.

In a preferred practice of the process, the oxidation steps are carried out together in an oxidation stage comprising one or more reactors, and the esterification steps are carried out together in an esterification stage comprising one or more reactors. This is referred to herein as the cooxidation process. Patents disclosing embodiments of the cooxidation process are the U.S. Pat. No. 2,772,305, to Levine et al., and the U.S. Pat., No. 2,894,978, to Katzschmann. katzschmann. In the commercial practice of the cooxidation process, which is done on a continuous basis, p-xylene is introduced into the oxidation stage, reaction mixture formed in the oxidation stage, herein referred to as oxidate, is introduced along with methanol into the esterification stage, reaction mixture formed in the esterification stage is separated by distillation into a distillate comprising DMT and methyl p-toluate, and a residue, and the distillate is separated into a methyl p-toluate fraction and a DMT fraction. The methyl p-toluate fraction is charged into the oxidation stage. The DMT fraction is treated to obtain DMT of the desired degree of purity. The residue in some instances is recycled through the oxidation stage with only a small proportion thereof being removed from the process. In other instances all of the residue is removed from the process.

In any event the oxidate is a complex mixture. It not only comprises p-toluic acid and monomethyl terephthalate, but other oxidation products as well. One such product is terephthalic acid. The presence of terephthalic acid in the oxidate indicates oxidation of p-toluic acid in the oxidation stage. That this takes place is supported by the U.S. Pat., No. 2,723,994, to Haefele et al., and British Patent specification 1,231,635.

A disadvantage of the commercial embodiment of the cooxidation process is the high amount of material recycled through the esterification stage and the oxidizer stage. This is necessary because of the relatively low conversion of oxidizable material to acid material in the oxidation stage. This disadvantage is reflected in the sizing of esterification and distillation equipment so as to have adequate capacity to accommodate the high amount of recycle material, in heat requirements in the esterification and distillation operations, and in a significant amount of recycle of DMT. In this latter aspect a certain amount of DMT is inevitably present in the methyl p-toluate fraction introduced into the oxidation stage, and in the residue separated from the esterification reaction mixture and returned to the oxidation stage.

One problem, therefore, to which this invention provides a solution, is how to reduce the amount of material recycled through the esterification stage to the oxidation stage.

In summary, this invention improves the prior art cooxidation process by separating a substantial portion, but not all, of the toluic acid from the oxidate prior to esterification, and returning at least a substantial part of the separated toluic acid to the oxidation stage. It is within the broader concepts of this invention to remove a portion of the separated toluic acid as a product of the process. However, this invention requires a substantial part of the separated toluic acid to be returned to the oxidation stage, and the material presented to the esterification stage for esterification to contain a substantial amount of toluic acid.

In one general embodiment of the improved process of this invention all of the oxidate is treated to separate therefrom a substantial portion of its toluic acid content without depleting that content to an insignificant concentration, and at least a substantial part of the separated toluic acid is returned to the oxidation stage.

In another general embodiment of the inventive process, which is the preferred general embodiment, only a portion of the oxidate is treated to separate toluic acid therefrom. This portion, which is referred to as the diverted portion, is generally about 20–70% by weight of the oxidate and preferably about 30–60% by weight of the oxidate. The remaining portion of the oxidate moves directly from the oxidation stage to the esterification stage or to a xylene stripping step which in one embodiment precedes the esterification stage.

In the preferred specific embodiments of the two general embodiments separation of toluic acid from oxidate is predicated on the fact that the temperature of the oxidate removed from the oxidation step is generally in a range from about 145° to about 200°C. and preferably in the range from about 160° to about 175°C. At temperatures in these ranges substantially all of the oxidation products in the oixdate, except terephthalic acid, are in solution. Moreover, these specific embodiments are predicated on the fact that toluic acid has a substantially lower crystallization temperature in the oxidate than either terephthalic acid or monomethyl terephthalate.

Thus, in the preferred specific embodiment of the general embodiment in which the entire oxidate is treated, the oxidate is cooled sufficiently to crystallize at least a substantial portion of its monomethyl terephthalate content and most of the small amount of dissolved terephthalic acid without crystallizing a substantial proportion of its toluic acid content. A substantial portion, but not all, of the mother liquid (the liquid portion of a solution that remains after crystallization takes place) is separated from the solids, at least part of the separated mother liquor is returned to the oxidation stage, and the remaining solids and mother liquor remaining after the separation are introduced into the esterification stage.

In the preferred specific embodiment of the general embodiment in which only part of the oxidate is treated according to the process of this invention, the diverted portion of the oxidate is cooled sufficiently to crystallize at least a substantial proportion of its monomethyl terephthalate content and most of the small amount of dissolved terephthalic acid without crystallizing a substantial portion of the toluic acid content, substantially all of the mother liquor is separated from the resulting solids, at least a substantial portion of the mother liquor is returned to the oxidation stage, and the remaining solids are introduced into the esterification stage. In this specific embodiment the consistency of the mother liquor may be too high to allow easy separation of solids therefrom in the solids separation step. In such event, preferably a quantity of xylene, which can be fresh xylene, condensed xylene, fraction stream from the oxidation stage, or both, is added to the diverted portion of the oxidate to give the mixture (preferably in the form of a slurry) resulting from the cooling step the desired degree of fluidity in the solids separation step. The quantity of xylene added can be as much as that normally charged to the oxidation stage without any necessity of stripping xylene from the mother liquor obtained in the ensuing solids separation step. Stated another way, the xylene feed to the oxidation stage can be introduced at this point in the improved process. Generally the quantity of p-xylene added to the oxidate is such that the resulting p-xylene concentration in the slurry is in the range from about 15 to about 80% by weight of the slurry and preferably in the range from about 25 to about 60 % by weight of the slurry.

In both specific embodiments the temperature at which the oxidate is finally established and maintained depends on the composition of the oxidate, and the amount of xylene, if any, added to it. The temperature must be high enough to avoid substantial precipitation of toluic acid. On the other hand, it preferably is low enough to crystallize most of the monomethyl terephthalate in the oxidate. Such temperature generally is in the range from about 60° to about 140°C. and preferably in the range from about 75° to about 130°C.

Separation of solids from the slurry in either specific embodiment is accomplished by any suitable procedure. The most practical procedure is a settlement procedure such as, for example, filtration, centrifugation or the like.

The solids obtained in the solids separation step, which consist essentially of terephthalic acid and monomethyl terephthalate, are charged to the esterification stage. In the general embodiment of the inventive process in which all of the oxidate is treated, the solids in one specific practice thereof first are slurried with a portion of the separated mother liquor or a xylene stripped portion of the separated mother liquor, and then charged to the esterification step. In another specific practice thereof the solids and a portion of the mother liquor or a xylene stripped portion of the mother liquor are separately charged to the esterification stage. In the general embodiment in which only part of the oxidate is treated, the solids are added to the untreated portion of the oxidate prior to xylene stripping or after xylene stripping, if such is practiced, or charged separately from the untreated portion of the oxidate or xylene stripped untreated portion of the oxidate to the esterification stage.

The best mode now contemplated for carrying out the invention is illustrated by the drawing which forms a material part of these disclosures, and which in brief depicts in diagrammatic fashion a flowsheet of a preferred specific embodiment of the inventive process for making DMT.

More particularly, the drawing illustrates a plant for the production of DMT. The plant comprises an oxidation stage 2, a xylene stripping stage 4, an esterification stage 6 and an ester (esterification reaction mixture) fractionation stage 8.

The oxidation stage 2 comprises one or more oxidation reactors in parallel or in series. Entering the oxidation stage are a fresh liquid p-xylene stream 10, a recycle liquid p-xylene stream 12, a molecular oxygen-bearing gas stream 14 (for example, air), an oxidation catalyst stream 16 (comprising a suitable oxidation catalyst, which also functions as an esterification catalyst in the esterification stage 6), a recycle residue stream 18, a methyl p-toluate fraction stream 20, and a condensed xylene fraction stream 22. These streams are brought together in the oxidation reactor or reactors under pressure, temperature and residence time conditions selected to give optimum conversion of oxidizable material to acid material. Leaving the oxidation stage are the condensed xylene fraction stream 22 and an oxidate stream 24 which goes to the xylene stripping stage 4.

The xylene stripping stage 4 comprises a distillation column which is operated so that substantially all of the xylene content of the oxidate stream is removed. Leaving the xylene stripping stage are the recycle p-xylene stream 12 and a xylene stripped oxidate stream 26 which goes to the esterification stage 6.

The esterification stage 6 comprises one or more esterification reactors. Also entering the esterification stage is a methanol stream 28. The esterification stage is operated under pressure, temperature and residence time conditions selected to give optimum conversion of acid material in that stage to methyl ester material. In addition to methyl ester material, water is formed in the esterification of the acid material. Hence, exiting the esterification stage 6 is an overhead stream 30 which comprises water. Esterification reaction mixture leaves the esterification stage by way of ester stream 32 which is introduced into the ester fractionation stage 8.

The ester fractionation stage 8 comprises one or more distillation columns. In a typical ester fractionation stage the ester stream is first separated by distillation into an overhead product and a bottom residue fraction, and the overhead product is separated by distillation into an overhead methyl p-toluate fraction and a bottom DMT fraction. In any event, leaving the ester fractionation stage 8 is a residue fraction stream 34, the methyl p-toluate fraction stream 20, and a DMT fraction stream 36. The DMT fraction stream is treated to obtain DMT with the desired degree of purity. The residue fraction stream 34 is divided into the recycle residue stream 18 (which is optional) and a purged residue stream 38.

Up to this point the plant as described is conventional.

However, under the concepts of this invention, between the oxidation stage 2 and the xylene stripping stage 4 is a toluic acid separation stage 40.

This stage comprises a crystallizer (not shown) and a centrifuge (not shown) or other solids-mother liquor separation means.

Entering the toluic acid separation stage 40 are a p-xylene stream 41, diverted oxidate stream 42 and a condensed xylene fraction stream 43 which is a diversion of part of the condensed xylene fraction stream 22 from the oxidation stage 2. In the toluic acid separation stage these streams are combined in the crystallizer and the resulting diluted oxidate is established therein at a temperature at which most of the monomethyl terephthalate crystallizes without substantial crystallization of toluic acid. Crystallization of monomethyl terephthalate and of the small amount of dissolved terephthalic acid is effected thereby. The resulting slurry is removed from the crystallizer and introduced into the centrifuge which is operated to separate the solids from the mother liquor.

Typical normal steady state flow rates and compositions of various streams in the plant of the drawing with and without any diversion of oxidate via diverted oxidate stream 42 to the toluic acid separation stage 40 and thus with and without any flow of the mother liquor stream 44 and TPA and MMT solids stream 46 are as follows, the flow rates being expressed as parts by weight, and the oxidation being carried out at 165°C. and 5 kilograms per square centimeter gauge pressure.

|  | Flow Rates | |
|---|---|---|
|  | Without Diversion | With Diversion |
| p-Xylene Stream 10 | 100 | 0 |
| Recycle Residue Stream 18 | 88 | 77 |
| Methyl p-Toluate Fraction Stream 20 | 174 | 91 |
| Oxidate Stream 24 | 445 | 428 (Before Diversion) |
| Diverted Oxidate Stream 42 | 0 | 214 |
| p-Xylene Stream 41 | 0 | 100 |
| Condensed Xylene Fraction Stream 43 | 0 | 49 |
| Mother liquor Stream 44 | 0 | 235 |
| TPA and MMT Solids Stream 46 | 0 | 128 |
| Stripped Oxidate Stream 26 | 382 | 274 |
| Ester Stream 32 | 412 | 297 |
| DMT Fraction Stream 36 | 157 | 157 |
| Purged Residue Stream 38 | 9 | 8 |

Compositions of various one of the streams under the above conditions are as follows, the symbol (—) designating a zero or insignificant concentration:

Without Diversion (% By Weight)

| Components | Oxidate Stream 24 | Ester Stream 32 |
|---|---|---|
| p-Toluic Acid | 17 | — |
| Terephthalic Acid | 9 | — |
| Monomethyl Terephthalate | 20 | — |
| Methyl p-Toluate | 24 | 39 |
| Xylene | 8 | — |
| DMT | 2 | 39 |
| Others | 20 | 22 |

With Diversion (% By Weight)

| Components | Oxidate Stream 24 | Condensed Xylene Fraction Stream 43 | Mother Liquor Stream 44 | TPA & MMT Solids Stream 46 | Combined Oxidate Stream 24 and TPA & MMT Solids Stream 46 | Ester Stream 32 |
|---|---|---|---|---|---|---|
| p-Toluic Acid | 23 | — | 16 | 8 | 17 | — |
| Terephthalic Acid | 16 | — | 0 | 27 | 20 | — |
| Monomethyl Terephthalate | 17 | — | 2 | 25 | 20 | — |
| Methyl p-Toluate | 17 | 10 | 14 | 7 | 13 | 31 |
| Xylene | 8 | 90 | 53 | 27 | 14.5 | — |
| DMT | 1 | — | 1 | 0 | 0.5 | 53 |
| Others | 18 | — | 14 | 6 | 15 | 16 |

Leaving the toluic acid separation stage 40 is a mother liquor stream 44 and a terephthalic acid (TPA) and monomethyl terephthalate (MMT) solids stream 46. The TPA and MMT solids stream 46 joins the oxidate stream 24 downstream from the diverted oxidate stream 42 and goes with the undiverted portion of the oxidate to the xylene stripping stage 4. The mother liquor stream 44 with its dissolved toluic acid content goes to the oxidation stage 2 in which it is combined in the oxidation reactor or reactors with the p-xylene streams 10 and 12, the molecular oxygen-bearing gas stream 14, the oxidation catalyst stream 16, recycle residue stream 18, the methyl p-toluate fraction stream 20, and the remaining part of the condensed xylene fraction stream 22.

From these data it can be seen that the stream presented to the esterification stage has a substantially increased acid content and a substantially decreased nonesterifiable material content, and that the amount of material which must be recycled from the ester fractionation stage has been sharply reduced. The apparent effect is an enrichment of the material subjected to esterification. Hence, the process of this invention can be referred to as an oxidate enrichment process.

Advantages obtained in modifying according to this invention an existing DMT plant are a substantial increase in the capacity of the esterification stage 6, a substantial increase in the capacity of the ester fractionation stage 8, a substantial reduction in the recycle of DMT because of the substantial reduction in the amounts of methyl p-toluate fraction and residue recycled through the oxidation stage, substantially higher oxidation catalyst level in the oxidation stage than in the esterification stage, and, because of reduced recycle, substantial energy savings.

Advantages of the process when incorporated into a new plant include an esterification stage 6 with substantially less required esterification capacity, an ester fractionation stage 8 with a substantially less required capacity, and substantially reduced heat requirements for the esterification and ester fractionation stages.

Thus, this invention provides a significant improvement in the production of DMT.

Other features, advantages and specific embodiments of this invention will become readily apparent to those exercising ordinary skill in the art after reading the foregoing disclosures. Such specific embodiments are within the scope of the claimed subject matter unless expressly indicated to the contrary by claim language. Moreover, while a specific embodiment of this invention has been described in considerable detail, variations and modifications of it can be effected without departing from the spirit and scope of the invention as disclosed and claimed.

I claim:

1. In the process for the production of dimethyl terephthalate in which an oxidate comprising p-toluic acid and monomethyl terephthalate is esterified with methanol to form a reaction mixture comprising methyl p-toluate and dimethyl terephthalate, methyl p-toluate is separated from said reaction mixture, and p-xylene and said methyl p-toluate are cooxidized in the liquid phase with molecular oxygen to form more oxidate which is treated as aforesaid, the improvement which comprises: separating a substantial portion, but not substantially all, of the p-toluic acid from said oxidate prior to said oxidate being esterified with methanol, and cooxidizing at least a substantial part of the separated p-toluic acid with said p-xylene and said methyl p-toluate.

2. The process according to claim 1 in which said p-xylene and said methyl p-toluate are cooxidized at about 145°–200°C. and p-toluic acid is separated from said oxidate by establishing at least a substantial portion of said oxidate in a crystallization temperature range in which monomethyl terephthalate crystallizes without substantial crystallization of p-toluic acid, separating mother liquor from the resulting solids and cooxidizing said mother liquor with said p-xylene and said methyl p-toluate.

3. In the process for the production of dimethyl terephthalate in which an oxidate comprising p-toluic acid and monomethyl terephthalate is esterified with methanol to form a reaction mixture comprising methyl p-toluate and dimethyl terephthalate, methyl p-toluate is separated from said reaction mixture, and p-xylene and said methyl p-toluate are cooxidized at about 145°–200°C. in the liquid phase with molecular oxygen to form more oxidate which is treated as aforesaid, the improvement which comprises: separating a substantial portion, but not substantially all, of the p-toluic acid from said oxidate prior to said oxidate being esterified with methanol, by establishing at least a substantial portion of said oxidate in a crystallization temperature range of about 60°–140°C., separating mother liquor from the resulting solids, and cooxidizing at least a substantial portion of said mother liquor with said p-xylene and said methyl p-toluate.

4. The process according to claim 3 in which about 20–70% by weight of said oxidate is established in said crystallization temperature range, and said solids and 80–30% by weight of said oxidate are coesterified with methanol.

5. The process according to claim 4 in which p-xylene is added to said 20–70% by weight of said oxidate prior to its being established in said crystallization temperature range.

6. The process according to claim 5 in which the quantity of p-xylene added is such that the p-xylene concentration in the resulting mixture of mother liquor and solids is about 15–80% by weight of said mixture.

7. The process according to claim 6 in which said p-xylene and said methyl p-toluate are cooxidized at about 160°–175°C., said crystallization temperature range is about 75–130°C., about 30–60% by weight of said oxidate is established in said crystallization temperature range and about 70–40% by weight of said oxidate and said solids are coesterified with methanol.

* * * * *